US012109017B2

(12) United States Patent
Strickland

(10) Patent No.: US 12,109,017 B2
(45) Date of Patent: Oct. 8, 2024

(54) REMOTELY TRACKING RANGE OF MOTION MEASUREMENT

(71) Applicant: August River, Ltd Co, North Augusta, SC (US)

(72) Inventor: William Lee Strickland, North Augusta, SC (US)

(73) Assignee: August River, Ltd Co, North Augusta, SC (US)

( * ) Notice: Subject to any disclaimer, the term of this patent is extended or adjusted under 35 U.S.C. 154(b) by 0 days.

(21) Appl. No.: 18/450,054

(22) Filed: Aug. 15, 2023

(65) Prior Publication Data

US 2024/0057893 A1    Feb. 22, 2024

Related U.S. Application Data

(60) Provisional application No. 63/398,822, filed on Aug. 17, 2022.

(51) Int. Cl.
| | |
|---|---|
| *A61B 5/11* | (2006.01) |
| *A61B 5/00* | (2006.01) |
| *A61B 5/107* | (2006.01) |
| *G06T 7/246* | (2017.01) |
| *G06T 7/60* | (2017.01) |

(Continued)

(52) U.S. Cl.
CPC .......... *A61B 5/1121* (2013.01); *A61B 5/1071* (2013.01); *A61B 5/1128* (2013.01); *A61B 5/4528* (2013.01); *A61B 5/7425* (2013.01); *G06T 7/246* (2017.01); *G06T 7/60* (2013.01); *G06T 7/70* (2017.01); *G06T 11/00* (2013.01); *G16H 40/67* (2018.01); *G06T 2200/28* (2013.01); *G06T 2207/10016* (2013.01); *G06T 2207/20092* (2013.01); *G06T 2207/30196* (2013.01); *G16H 10/60* (2018.01)

(58) Field of Classification Search
None
See application file for complete search history.

(56) References Cited

U.S. PATENT DOCUMENTS

| | | |
|---|---|---|
| 6,007,459 A | 12/1999 | Burgess |
| 2006/0098090 A1 | 5/2006 | Bernard et al. |

(Continued)

OTHER PUBLICATIONS

International Search Report and Written Opinion mailed Dec. 7, 2023 cited in Application No. PCT/US23/72303, 9 pgs.

*Primary Examiner* — Benjamin S Melhus
(74) *Attorney, Agent, or Firm* — BEKIARES ELIEZER LLP

(57) ABSTRACT

A platform for monitoring range of motion in a joint includes initiating a range of motion monitoring application and connecting the application to a video communication platform. Video data, comprising the joint of the patient, is received from the communication platform. The platform may be used to determine that the patient is in position for calculating a range of motion of the joint, and capture an image of the joint from the received video data. The platform receives, from a user, a selection of a first set of points used in measuring range of motion, and calculates a first angle measurement associated with the range of motion of the joint based on the selected set of points. The captured image is displayed together with an overlay comprising the first set of points and the first calculated angle, and the captured image and the overlay are stored to a storage device.

14 Claims, 5 Drawing Sheets

(51) Int. Cl.
*G06T 7/70* (2017.01)
*G06T 11/00* (2006.01)
*G16H 40/67* (2018.01)
*G16H 10/60* (2018.01)

(56) References Cited

U.S. PATENT DOCUMENTS

| | | | |
|---|---|---|---|
| 2011/0039659 | A1 | 2/2011 | Kim et al. |
| 2013/0226039 | A1 | 8/2013 | Shani et al. |
| 2013/0230211 | A1* | 9/2013 | Tanabiki .................. G06T 7/75 |
| | | | 382/103 |
| 2014/0147820 | A1 | 5/2014 | Snow et al. |
| 2014/0228985 | A1* | 8/2014 | Elliott ...................... A61B 5/11 |
| | | | 700/91 |
| 2014/0276095 | A1 | 9/2014 | Griggs et al. |
| 2015/0005910 | A1* | 1/2015 | Ishii ...................... G06V 40/23 |
| | | | 700/91 |
| 2015/0130841 | A1* | 5/2015 | Kohli .................... G16H 20/30 |
| | | | 345/633 |
| 2015/0133820 | A1* | 5/2015 | Zohar .................... G16H 20/30 |
| | | | 600/595 |
| 2015/0310629 | A1* | 10/2015 | Utsunomiya .......... G06V 10/34 |
| | | | 382/107 |
| 2016/0249866 | A1* | 9/2016 | Ring ..................... A61B 5/1114 |
| | | | 600/595 |
| 2017/0147789 | A1* | 5/2017 | Wiedenhoefer ........ A61B 1/041 |
| 2018/0020954 | A1* | 1/2018 | Lillie .................... A61B 5/4585 |
| | | | 600/476 |
| 2019/0038187 | A1* | 2/2019 | Latella, Jr. ............. G06F 3/0346 |
| 2019/0066832 | A1* | 2/2019 | Kang .................. A61B 5/1128 |
| 2019/0117129 | A1* | 4/2019 | Slepian ................ A61B 5/1071 |
| 2020/0155900 | A1 | 5/2020 | Takagi et al. |
| 2021/0052199 | A1* | 2/2021 | Park ..................... A61B 5/4561 |
| 2021/0307650 | A1* | 10/2021 | Barr ..................... A61B 5/1121 |
| 2021/0322856 | A1* | 10/2021 | Virkar ....................... G06T 7/73 |
| 2022/0005187 | A1 | 1/2022 | Lyman et al. |
| 2022/0176200 | A1* | 6/2022 | Jiang ................. A63B 24/0021 |
| 2022/0215909 | A1* | 7/2022 | Raj ........................ G16H 15/00 |

\* cited by examiner

REMOTELY TRACKING RANGE OF MOTION MEASUREMENT

RELATED APPLICATION

This application claims the benefit of priority to U.S. Provisional Application No. 63/398,822 on filed Aug. 17, 2022, which is hereby incorporated by reference herein in its entirety.

It is intended that the above-referenced application may be applicable to the concepts and embodiments disclosed herein, even if such concepts and embodiments are disclosed in the referenced applications with different limitations and configurations and described using different examples and terminology.

FIELD OF DISCLOSURE

The present disclosure generally relates to distribution of health-related services via electronic communication technologies, and particularly to monitoring of active range of motion measurements taken electronically via electronic communication technologies.

BACKGROUND

In some situations, a user may need medical services, but traveling to a doctor may be difficult dangerous, impractical, or undesirable for one or more reasons (e.g., environmental factors, personal health factors, etc.). In such cases, telehealth visits provide for distribution of health-related services and health information via electronic communication technologies, such as the Internet. In particular wellness visits, such as follow-up visits for medical procedures, may be good candidates for telehealth appointments, as there is little for a doctor or other medical professional to do other than to visually inspect the healing process.

For some patients, the visual inspection process may include measuring a range of motion for a particular joint. Typically, range of motion may be measured with a goniometer, which includes one stationary arm one movable arm, and a fulcrum that includes a measuring scale. Typically goniometer measurements require an in-person (rather than telehealth) visit, since the device must contact the patient at the joint where range of motion is being measured.

Accordingly, there is a need for a way to measure patient range of motion via a telehealth session.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

A computer-implemented method for monitoring range of motion in a joint of a patient's body includes initiating range of motion monitoring application and connecting the application to a video communication session. The method includes receiving a user selection of a template for range of motion measurement and providing instructions to a patient regarding body positioning. The method may include capturing an image of at least a portion of a patient's body. The method may further include receiving selection of a plurality of reference points on the captured image, the plurality of reference points comprising: a first point associated with a stationary portion of the patient's body, a second point associated with a movable part of the patient's body, and a third point associated with a fulcrum connection the stationary portion to the movable portion. Angle calculations based on the plurality of selected reference points may be computed, and the computed angle on the captured image. Finally, the captured image with the overlay may be stored.

In embodiments, the platform comprises a system, method, and/or computer program product configured to receive video data from a communication platform, the video data comprising the joint of the patient and determine that the patient is in position for calculating a range of motion of the joint. Responsive to determining that the patient is in position, the platform may capture an image of the joint from the received video data, and receive, from a user, selection of a first set of points on the image used in measuring range of motion. The platform may calculate a first angle measurement associated with the range of motion of the joint based on the selected set of points, and may display the captured image together with an overlay comprising the first set of points and the first calculated angle. The platform may store the captured image and the overlay to a storage device.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1:
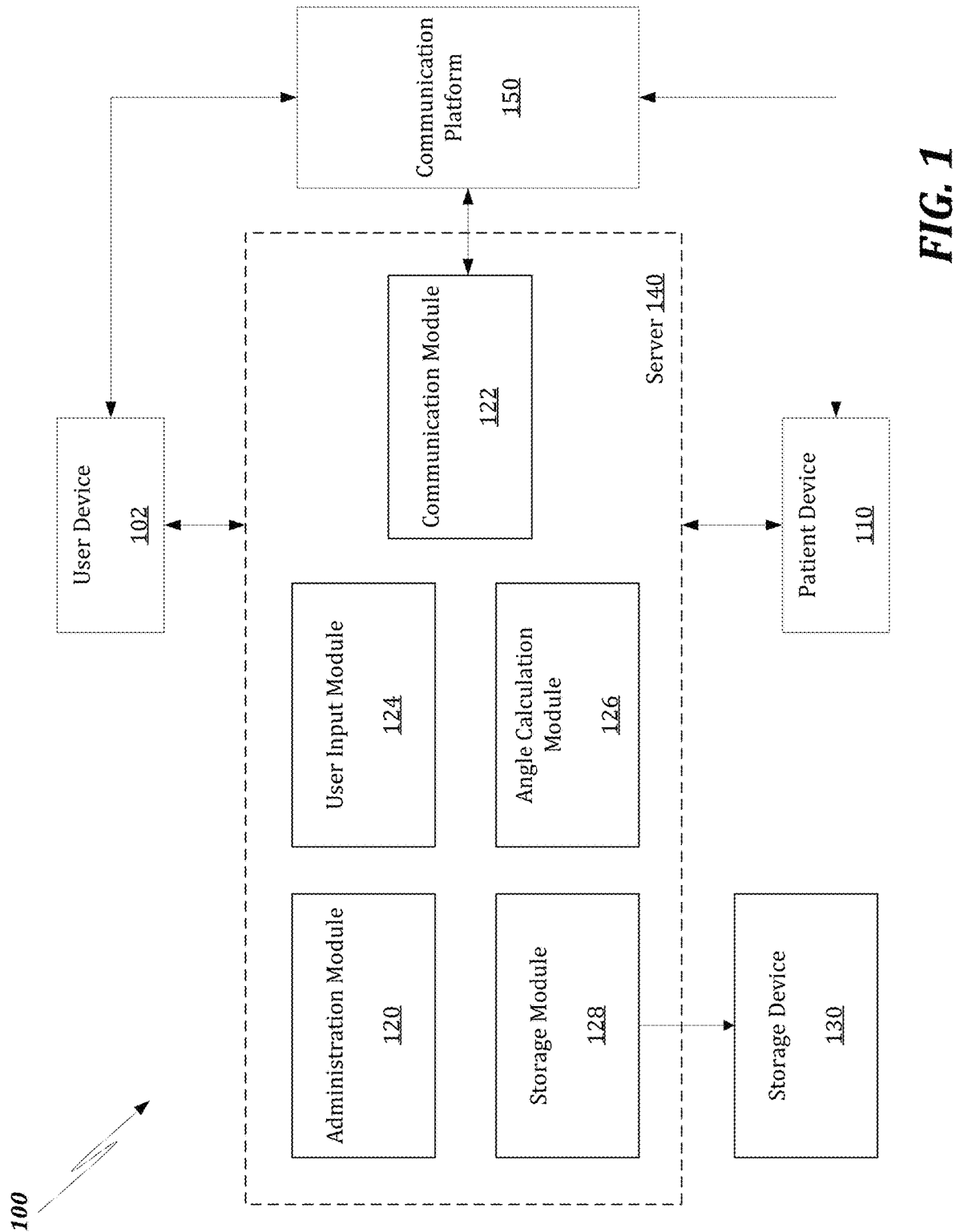
FIG. 1 illustrates a block diagram of an operating environment of a range of motion measurement tracking platform consistent with the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely to provide a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such a term to mean based on the contextual use of the term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subject matter disclosed under the header.

The present disclosure includes many aspects and features. Moreover, while many aspects and features relate to, and are described in, the context of tracking range of motion measurement, embodiments of the present disclosure are not limited to use only in this context.

I. Platform Overview

This overview is provided to introduce a selection of concepts in a simplified form that are further described below. This overview is not intended to identify key features or essential features of the claimed subject matter. Nor is this overview intended to be used to limit the claimed subject matter's scope.

The system allows a patient and a health care professional (e.g., a doctor, a nurse, a physical therapist, and/or the like) to establish a video communication session using a known communication platform, such as (but not limited to) RingCentral, Google Meet, Apple FaceTime, Zoom, Skype, GoToMeeting, etc. In embodiments, the health care professional may select a particular template from the system for capturing the measurement from the patient. Selecting the template may including choosing a template from a list of available templates, creating a new template, or determining that no template is applicable to the needed measurement.

The health care professional may guide the patient to assuming particular position based at least in part on the joint in which range of motion is to be measures. Guiding the patient into a particular position may include providing oral and/or visual instructions to the patient. In some embodiments, the system may store instructions to be provided to the patient. These instructions may be based on the patient location, the patient joint being examined for range of motion monitoring, the patient's general physical abilities (e.g., whether or not the patient is capable of standing), the health care professional preferences, etc.

The health care professional may, during the patient's movement, capture one or more images, and may calculate an angle formed by the joint. For example, the health care professional may select a first point associated with a first portion of the patient's body, a second point associated with a second portion of the patient's body that is movable relative to the first portion, and a third point associated with a fulcrum that connects the first portion the second portion. In embodiments, the system may determine an angle between the first point and the second point, measured about the fulcrum. In embodiments, the system may draw the angle measured on the captured image. In some embodiments, the angle may be overlayed on the joint.

The system may be configured to store the captured images to a HIPPA-compliant storage medium, such as an electronic medical record system. Additionally or alternatively, the health care professional may store screenshots locally, at computer associated with the health care professional. To store screenshots locally, the system may obfuscate or obscure patient identifying information (PII), including (but not limited to) applying a blur filter to the image prior to storing the image. In embodiments, the image itself may be obfuscated, without obfuscating the angle drawn on the image.

In some embodiments, the system may allow the health care professional to select one or more additional reference points on the captured image, and may perform additional calculations based on the additional captured reference points. The system may allow for capture of additional images of the patient, and may allow the health care professional to select one or more reference points on the additional images and perform calculations based on the reference points on the additional images. In some embodiments, the system may be configured to compare multiple captured images from the same patient to compare the images to one another. Such comparison may show changes in range of motion over time, and/or may illustrate a full range of motion of a joint (e.g., extreme flexure and extreme extension).

The system may purge images and data gathered that include PII. For example, the system may cause a "clipboard" or cache associated with a computer used by the health care professional to be purged or deleted. The communication between the health care professional and the patient may be terminated by using session controls outside the system (e.g., controls associated with the communication platform).

Embodiments of the present disclosure may comprise methods, systems, and a computer readable medium comprising, but not limited to, at least one of the following:
A. A UI Layer;
B. An API Layer;
C. An Administration Layer;
D. A Protocol Layer;

Details with regards to each module are provided below. Although modules are disclosed with specific functionality, it should be understood that functionality may be shared between modules, with some functions split between modules, while other functions duplicated by the modules. Furthermore, the name of each module should not be construed as limiting upon the functionality of the module. Moreover, each component disclosed within each module can be considered independently, without the context of the other components within the same module or different modules. Each component may contain functionality defined in other portions of this specification. Each component disclosed for one module may be mixed with the functionality of other modules. In the present disclosure, each component can be claimed on its own and/or interchangeably with other components of other modules.

The following depicts an example of a method of a plurality of methods that may be performed by at least one of the aforementioned modules, or components thereof. Various hardware components may be used at the various stages of the operations disclosed with reference to each module. For example, although methods may be described to be performed by a single computing device, it should be understood that, in some embodiments, different operations may be performed by different networked elements in operative communication with the computing device. For example, at least one computing device 400 may be employed in the performance of some or all of the stages disclosed with regard to the methods. Similarly, an apparatus may be employed in the performance of some or all of the stages of the methods. As such, the apparatus may comprise at least those architectural components as found in computing device 400.

Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in orders that differ from the ones disclosed below. Moreover, various stages may be added or removed without altering or departing from the fundamental scope of the depicted methods and systems disclosed herein.

Consistent with embodiments of the present disclosure, a method may be performed by at least one of the modules disclosed herein. The method may be embodied as, for example, but not limited to, computer instructions which, when executed, perform the method. The method may comprise the following stages:

Initiating range of motion monitoring application;
Connecting application to a video communication session;
Selecting template for range of motion measurement;
Providing instructions to patient regarding body positioning;
Capturing an image of at least a portion of a patient's body;
Selecting a plurality of reference points on the captured image, the plurality of reference points comprising:
a first point associated with a stationary portion of the patient's body,
a second point associated with a movable part of the patient's body, and
a third point associated with a fulcrum connection the stationary portion to the movable portion;
Computing angle calculations based on the plurality of selected reference points;
Overlaying the computed angle on the captured image; and
Storing the captured image with the overlay.

Although the aforementioned method has been described to be performed by a range of motion monitoring platform 100, it should be understood that computing device 400 may be used to perform the various stages of the method, and/or may be a portion of the platform 100. Furthermore, in some embodiments, different operations may be performed by different networked elements in operative communication with computing device 400. For example, a plurality of computing devices may be employed in the performance of some or all of the stages in the aforementioned method. Moreover, a plurality of computing devices may be configured much like a single computing device 400. Similarly, an apparatus may be employed in the performance of some or all stages in the method. The apparatus may also be configured much like computing device 400.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and subcombinations described in the detailed description.

II. Platform Configuration

FIG. 1 illustrates one possible operating environment through which a platform consistent with embodiments of the present disclosure may be provided. By way of non-limiting example, a range of motion monitoring platform 100 may be hosted on, for example, a cloud computing service. In some embodiments, the platform 100 may be hosted on a computing device 400. A user may access platform 100 through a software application and/or hardware device. The software application may be embodied as, for example, but not be limited to, a website, a web application, a desktop application, and a mobile application compatible with the computing device 400. One possible embodiment of the software application and/or hardware device may be provided by the Movement Measure™ suite of products and services.

The platform 100 may facilitate communication between a user device 102 associated with a health care professional and a patient device 110 associated with a patient. The platform 100 may include an administration module 120, a communication module 122, a user input module 124, an angle measurement module 126, and a storage module 128. One or more of the modules may be embodied on a server 140. In embodiments, the platform 100 may further include a storage device 130, a communication platform 150, and/or an administrative portal 160.

Accordingly, embodiments of the present disclosure provide a software and hardware platform comprised of a distributed set of computing elements, including, but not limited to:

A. Administration Module

The administration module 120 may include hardware and/or software configured to register and/or authenticate the platform 100 and/or one or more users of the platform 100 (e.g., the user device 102 and/or the patient device 110). In some embodiments, the administration module 120 may be configured to verify an installation of software onto a computing device (e.g., the computing device 400). In some embodiments, the administration module 120 may be configured to verify a user identifier and password associated with a user. In some embodiments, the administration module 120 may be configured to verify a biometric identifier (e.g., a fingerprint, a retinal scan, a facial scan, etc.) of the user.

Figure 2:
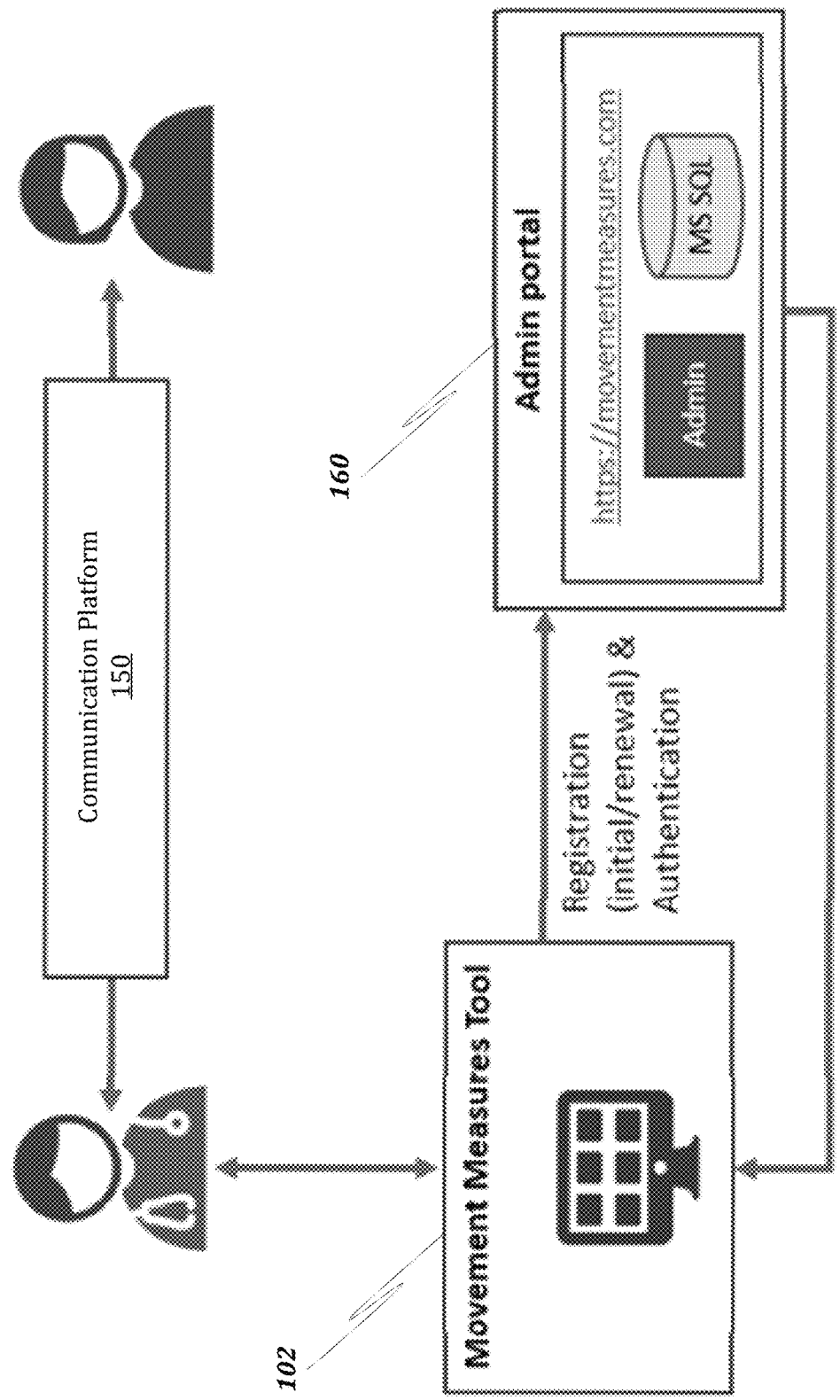
FIG. 2 illustrates a data flow within platform of FIG. 1 during an authentication process.

FIG. 2 shows an example of the registration and/or authentication process. During registration, a user (e.g., a healthcare provider) may use the user device 102 to establish an account for the platform 100 via a website, application, program, and/or the like. The user may provide, via the user device 102, authentication information, such as a user identifier, password, biometric identifier, and/or the like. The user device 102 may transmit the authentication information to an administrative portal 160 for storage therein (e.g., in a user database). Once registered, a user may authenticate by providing authentication information via the user device 102 to be verified by the administrative portal 160. In addition to establishing a connection between the user device 102 and the administrative portal 160. The user may also establish communication with a patient via the communication platform 150.

B. Communication Module

The communication module 122 may include hardware and/or software configured to provide a communication interface between the platform 100 and a communication platform 150, such as (but not limited to) an external communication platform (e.g., RingCentral, Google Meet, Apple FaceTime, Zoom, Skype, GoToMeeting, etc.) and/or an integrated proprietary communication platform facilitate video, audio, text, and/or data communication between the user device 102 and the patient device 110. Where the communication platform 150 comprises an external communication platform, the communication module 122 may include one or more application program interfaces (APIs) for allowing the external communication platform to share data (e.g., video data) with the platform 100. In embodiments, the communication module 122 may receive the shared data and cause display of the received data in an application operating on the platform 100, such that the received data is displayed in the platform application associated with the user device 102 and/or the patient device 110. In embodiments, the communication module 122 may further be configured to capture a snapshot (e.g., a still frame image) from the data received from the communication platform 150.

C. User Input Module

The user input module 124 may include hardware and/or software configured to receive input from a user device 102 associated with the platform 100 (e.g., a health care professional). The input may include a selection of a template for aiding the health care professional in positioning a patient. In embodiments, the input may comprise selection of a plurality of reference points on an image captured by the communication module. For example, the user may select at least a first point associated with a first portion of the patient's body, a second point associated with a second portion of the patient's body that is movable relative to the first portion, and a third point associated with a fulcrum that connects the first portion the second portion.

In some embodiments, the user input module 124 may create and display an overlay for the captured image that shows the selected reference points and one or more angles described by the captured reference points.

In some embodiments, the user input module 124 may create an and display overlay for the image showing one or more angle measurements arrayed around the fulcrum, in the style of a goniometer. The angle measurement indicators may be useful in documenting initial and subsequent range of motion for a joint of a patient.

D. Angle Calculation Module

The angle calculation module 126 may include hardware and/or software configured to receive the plurality of reference points captured by the user input module 124 and determine one or more angle measurements representing a range of motion of a joint based on the reference points. For example, the plurality of reference points may include a first point associated with a first portion of the patient's body, a second point associated with a second portion of the patient's body that is movable relative to the first portion, and a third point associated with a fulcrum that connects the first portion the second portion. In embodiments, the angle calculation module 126 may determine an angle between the first point and the second point, measured about the fulcrum. The determined angle may be an acute angle, right angle, obtuse angle, or reflex angle. In some embodiments, the angle calculation module may measure the angle between the first point and the second point, measured about the fulcrum, a complementary angle (e.g., an angle that, when added to the measured angle, equals 90°), a supplementary angle (e.g., an angle that, when added to the measured angle, equals 180°), and/or an explementary or conjugate angle (e.g., an angle that, when added to the measured angle, equals 360°).

In some embodiments, the angle calculation module 126 may calculate the one or more angles multiple times. For example, the user may calculate the one or more angles a plurality of times during a single session. The angle calculation module 126 may, for each calculated angle, create one or more average (e.g., mean, median, mode, weighted average, etc.) measurements over the session. As a particular example, where the angle measurement module 126 calculates the angle and the complementary angle, a user may take three measurements over the course of a session, with the measured angles being 130, 135, and 137, and the complementary angles being 50, 45, and 43. The angle calculation module 126 may compute a mean measured angle of 134, and a mean complementary angle of 46.

In some embodiments, the angle calculation module 126 may compare the calculated angle and or the calculated average angle to additional data. For example, the calculated angle may be compared to an angle associated with an average range of motion for the joint being measured, and/or with past measurements for the same joint from the same user.

E. Storage Module

The storage module 128 may include hardware and/or software configured to store the captured image to a storage device 130. In embodiments, the storage module 128 may store the captured image with the overlay. In embodiments, the captured image may be stored to a HIPPA-compliant storage system, such as an electronic medical record system. In some embodiments, the captured image may be stored to a computing device associated with the health care processional. The storage module 128 may obfuscate or obscure patient identifying information (PII), including (but not limited to) applying a blur filter to the image prior to storing the image. In embodiments, the image itself may be obfuscated, without obfuscating the angle drawn on the overlay.

In some embodiments, the storage module 128 may store the angle data calculated by the angle calculation module in association with the captured image. For example, both the image and the angle data may be stored to an electronic medical record associated with the patient in the storage device 130. In embodiments, one or more of the modules may be embodied on a server 140.

III. Platform Operation

Embodiments of the present disclosure provide a hardware and software platform operative by a set of methods and computer-readable media comprising instructions configured to operate the aforementioned modules and computing elements in accordance with the methods. The following depicts an example of at least one method of a plurality of methods that may be performed by at least one of the aforementioned modules. Various hardware components may be used at the various stages of operations disclosed with reference to each module.

For example, although methods may be described as being performed by a single computing device, it should be understood that, in some embodiments, different operations may be performed by different networked elements in operative communication with the computing device. For example, at least one computing device 400 may be employed in the performance of some or all of the stages disclosed with regard to the methods. Similarly, an apparatus may be employed in the performance of some or all of the stages of the methods. As such, the apparatus may comprise at least those architectural components found in computing device 400.

Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones described below. Moreover, various stages may be added or removed from the without altering or departing from the fundamental scope of the depicted methods and systems disclosed herein.

A. Remote Range of Motion Measurement Method

Consistent with embodiments of the present disclosure, a method 300 may be performed by at least one of the aforementioned modules. The method may be embodied as, for example, but not limited to, computer instructions, which, when executed, perform the method. The method may comprise the following stages:

The method allows a patient and a health care professional (e.g., a doctor, a nurse, a physical therapist, and/or the like) to establish a video communication session using a known communication platform, such as (but not limited to) RingCentral, Google Meet, Apple FaceTime, Zoom, Skype, GoToMeeting, etc. In embodiments, the health care professional may select a particular template from the system for capturing the measurement from the patient. Selecting the template may including choosing a template from a list of available templates, creating a new template, or determining that no template is applicable to the needed measurement.

The health care professional may guide the patient to assuming particular position based at least in part on the joint in which range of motion is to be measures. Guiding the patient into a particular position may include providing oral and/or visual instructions to the patient. In some embodiments, the system may store instructions to be provided to the patient. These instructions may be based on the patient location, the patient joint being examined for range of motion monitoring, the patient's general physical abilities (e.g., whether or not the patient is capable of standing), the health care professional preferences, etc.

The health care professional may, during the patient's movement, capture one or more images, and may calculate an angle formed by the joint. For example, the health care professional may select a first point associated with a first portion of the patient's body, a second point associated with a second portion of the patient's body that is movable relative to the first portion, and a third point associated with a fulcrum that connects the first portion the second portion. In embodiments, the system may determine an angle between the first point and the second point, measured about the fulcrum. In embodiments, the system may draw the angle measured on the captured image. In some embodiments, the angle may be overlayed on the joint.

The system may be configured to store the captured images to a HIPPA-compliant storage medium, such as an electronic medical record system. Additionally or alternatively, the health care professional may store screenshots locally, at computer associated with the health care professional. To store screenshots locally, the system may obfuscate or obscure patient identifying information (PII), including (but not limited to) applying a blur filter to the image prior to storing the image. In embodiments, the image itself may be obfuscated, without obfuscating the angle drawn on the image.

In some embodiments, the system may allow the health care professional to select one or more additional reference points on the captured image, and may perform additional calculations based on the additional captured reference points. The system may allow for capture of additional images of the patient, and may allow the health care professional to select one or more reference points on the additional images and perform calculations based on the reference points on the additional images. In some embodiments, the system may be configured to compare multiple captured images from the same patient to compare the images to one another. Such comparison may show changes in range of motion over time, and/or may illustrate a full range of motion of a joint (e.g., extreme flexure and extreme extension).

The system may purge images and data gathered that include PII. For example, the system may cause a "clipboard" or cache associated with a computer used by the health care professional to be purged or deleted. The communication between the health care professional and the patient may be terminated by using session controls outside the system (e.g., controls associated with the communication platform).

Figure 3:
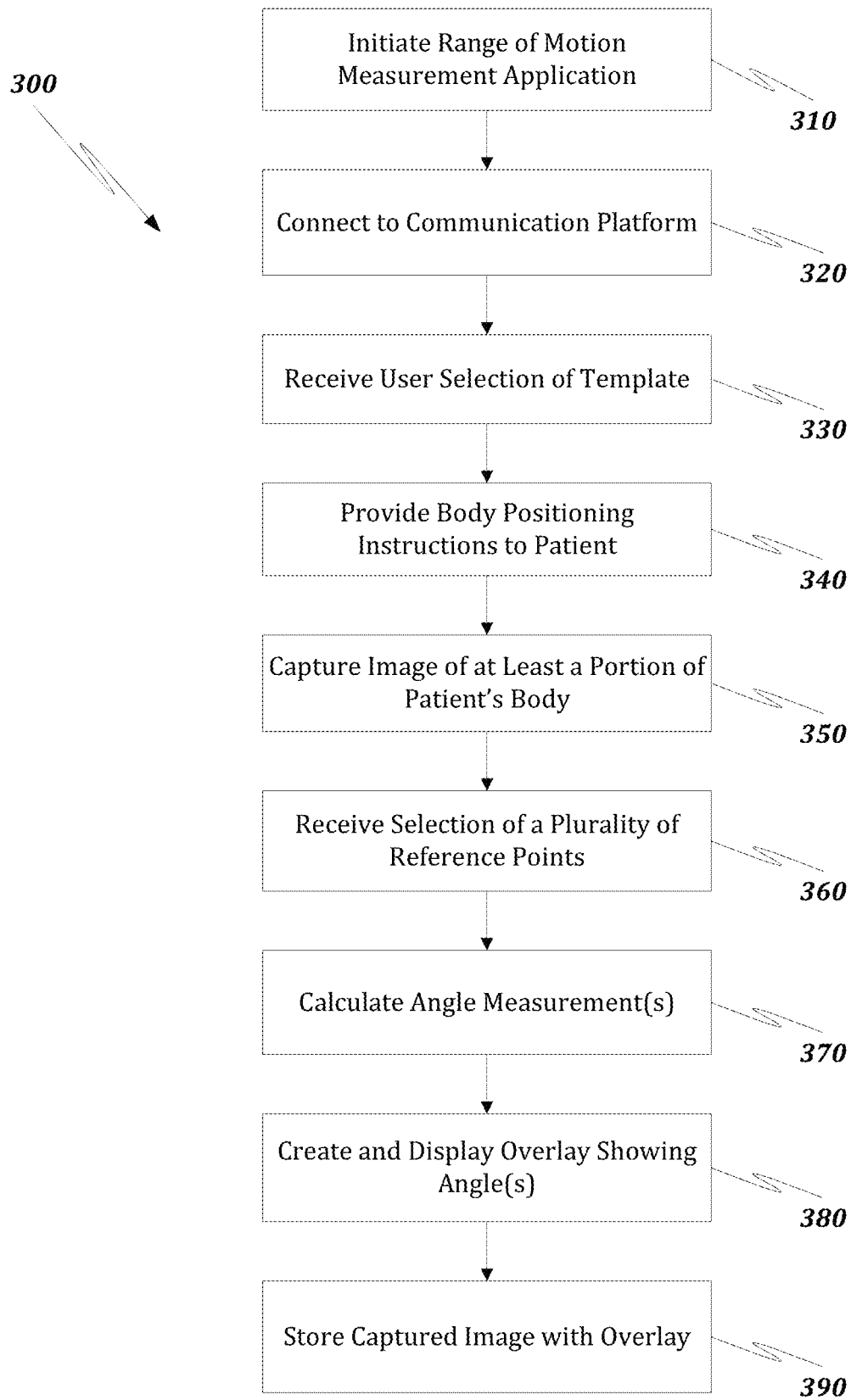
FIG. 3 is a flow chart of a method for providing remote tracking for range of motion measurement.

FIG. 3 is a flow chart setting forth the general stages involved in a method 300 consistent with an embodiment of the disclosure for providing range of motion monitoring platform 100. Method 300 may be implemented using a computing device 400 or any other component associated with platform 100 as described in more detail below with respect to FIG. 4. For illustrative purposes alone, computing device 400 is described as one potential actor in the following stages.

Method 300 may begin at stage 310, where computing device 400 may initiate or otherwise begin execution of a range of motion monitoring application. For example, a user (e.g., a health care professional, such as a physician, a nurse, or a physical therapist may actuate an icon associated with the range of motion monitoring application. Actuation of the icon may cause the range of motion monitoring application to begin execution. In embodiments, initiating the application may comprise providing login credentials for the application, such as a username and password, a biometric identifier (e.g., a fingerprint, a retinal scan, a facial scan, etc.), and/or the like. The system may verify the credentials before proceeding.

In stage 320, the computing device may initiate a video communication session between the user (a healthcare professional) and a patient. The video communication session may be initiated using a third party communication platform, such as (but not limited to) RingCentral, Google Meet, Apple FaceTime, Zoom, Skype, GoToMeeting, etc. The computing device may establish a connection to the third party communication platform through which the system may receive data. For example, the system may include one or more APIs for receiving information from the third party communication platform.

From stage 320, where computing device 400 initiates a video communication session between the user and a patient, method 300 may advance to stage 330, where the computing device 400 may receive, from the user, a selection of a template for range of motion measurement. For example, the computing device may enable a user to select a template from a list of available templates, to provide a custom template for use during the session, and/or to indicate that the user does not wish to use a template. In some embodiments, the template may comprise an overlay (e.g., a semi-opaque overlay) that may be useful to the user and/or the patient in assisting the patient in adjusting posture and placement for conducting a range of motion measurement. As a specific example, when the user needs to monitor range of motion in a patient's joint. As one non-limiting example, when monitoring range of motion in a patient's wrist, the user may select a template marked "Wrist". The selected template may show a semi-opaque outline of a patent with their elbow and wrist flat on a surface (e.g., a table), and the patient's hand bent upward from the table as far as possible.

Following selection of the template, the method 200 may proceed to stage 340, where the computing device may facilitate provision of instructions from the user to the patient regarding body positioning for the range of motion measurement. In embodiments, the instructions may be provided via audio and/or visual instructions form the user, via the third party communication platform. In some embodiments, the user may provide the instructions to the patient, and the computing device may deliver the instructions to the patient using the communications platform Alternatively or additionally, the computing device 400 may provide instructions to the user based on the template selected in stage 230. For example, the computing device 400 may display the template and/or provide audio and/or textual instructions regarding patient positioning. In some embodiments, the computing device may provide, to the user and/or the patient, feedback indicating when the patient is in correct position. For example, the feedback may include visual feedback (e.g., a change of color in the displayed template, etc.) and/or audio feedback (e.g., a chime or tone).

In stage 350, the computing device 400 may capture an image of the patient for range of motion analysis. For example, the computing device 400 may receive information from the communication platform and display the received information to the user. The user may determine that the patient is in a proper position, and provide an instruction to the computing device that causes the computing device to capture an image. In embodiments, the captured image may be displayed for the user.

In stage 360, the computing device 400 may receive a user selection of a plurality of reference points on the captured image. For example, the plurality of reference points may include at least a first point associated with a stationary portion of the patient's body, a second point associated with a movable part of the patient's body, and a third point associated with a fulcrum connection the stationary portion to the movable portion. Continuing the specific example, when measuring range of motion in a patient's wrist, the user may select a first point at the patient's elbow (e.g., resting on a table), a second point at the user's hand (e.g., flexed upward and off the table), and a third (fulcrum) point at the user's wrist. Those of skill in the art will recognize that more, fewer and/or different reference points may be included in the plurality of reference points without departing from the scope of the invention.

In stage 370, the computing device 400 may calculate one or more angle measurements based on the selected reference points. For example, given the example reference points discussed above, the computing device 400 may calculate an angle about the fulcrum point between the first point and the second point. In some embodiments, the computing device may further calculate a complementary angle (e.g., an angle that, when added to the measured angle, equals 90°), a supplementary angle (e.g., an angle that, when added to the measured angle, equals 180°), and/or an explementary or conjugate angle (e.g., an angle that, when added to the measured angle, equals 360°).

The user may perform steps 350-370 one or more times. Where steps 350 to 370 are performed more that once during a single session with the patient, the computing device may, for each calculated angle, create one or more average (e.g., mean, median, mode, weighted average, etc.) measurements over the session. As a particular example, where the computing device calculates the angle and the complementary angle, a user may take three measurements over the course of a session, with the measured angles being 130, 135, and 137, and the complementary angles being 50, 45, and 43. The computing device may compute a mean measured angle of 134, and a mean complementary angle of 46.

In stage 380, the computing device 400 may create an overlay on the captured image. The overlay may include the one or more reference points selected by the user, a drawing of the angle formed by the selected reference points, and/or the one or more calculated angles based on the selected reference points. In some embodiments, the overlay may include one or more angle measurement indicators arrayed around the fulcrum in a circular pattern, in the style of a goniometer. The angle measurement indicators may be useful in documenting initial and subsequent range of motion for a joint of a patient. The overlay may be displayed to the user and/or the patient on top of the captured image.

In stage 390, the computing device 400 may store the captured image with the overlay. In some embodiments, the captured image may be stored to a HIPPA-compliant storage medium, such as an electronic medical record system. Additionally or alternatively, the captured images may be stored locally, at a computer associated with the health care professional. To store screenshots locally, the system may obfuscate or obscure patient identifying information (PII), including (but not limited to) applying a blur filter to the image prior to storing the image. In embodiments, the image itself may be obfuscated, without obfuscating the image overlay (e.g., the one or more reference points, the angle drawn based on the reference points, and/or the angle measurements.

In some embodiments, the method 200 may allow the health care professional to capture additional images of the patient, and may allow the health care professional to select one or more reference points on the additional images and perform calculations based on the reference points on the additional images. In some embodiments, the system may be configured to compare multiple captured images from the same patient to compare the images to one another. Such comparison may show changes in range of motion over time, and/or may illustrate a full range of motion of a joint (e.g., extreme flexure and extreme extension).

Upon exiting the application, the system may purge images and data gathered that include PII. For example, the system may cause a "clipboard" or cache associated with a computer used by the health care professional to be purged or deleted. The communication between the health care professional and the patient may be terminated by the computing device 400, and/or by the user and/or the patient using session controls outside the system (e.g., controls associated with the communication platform).

Figure 5:
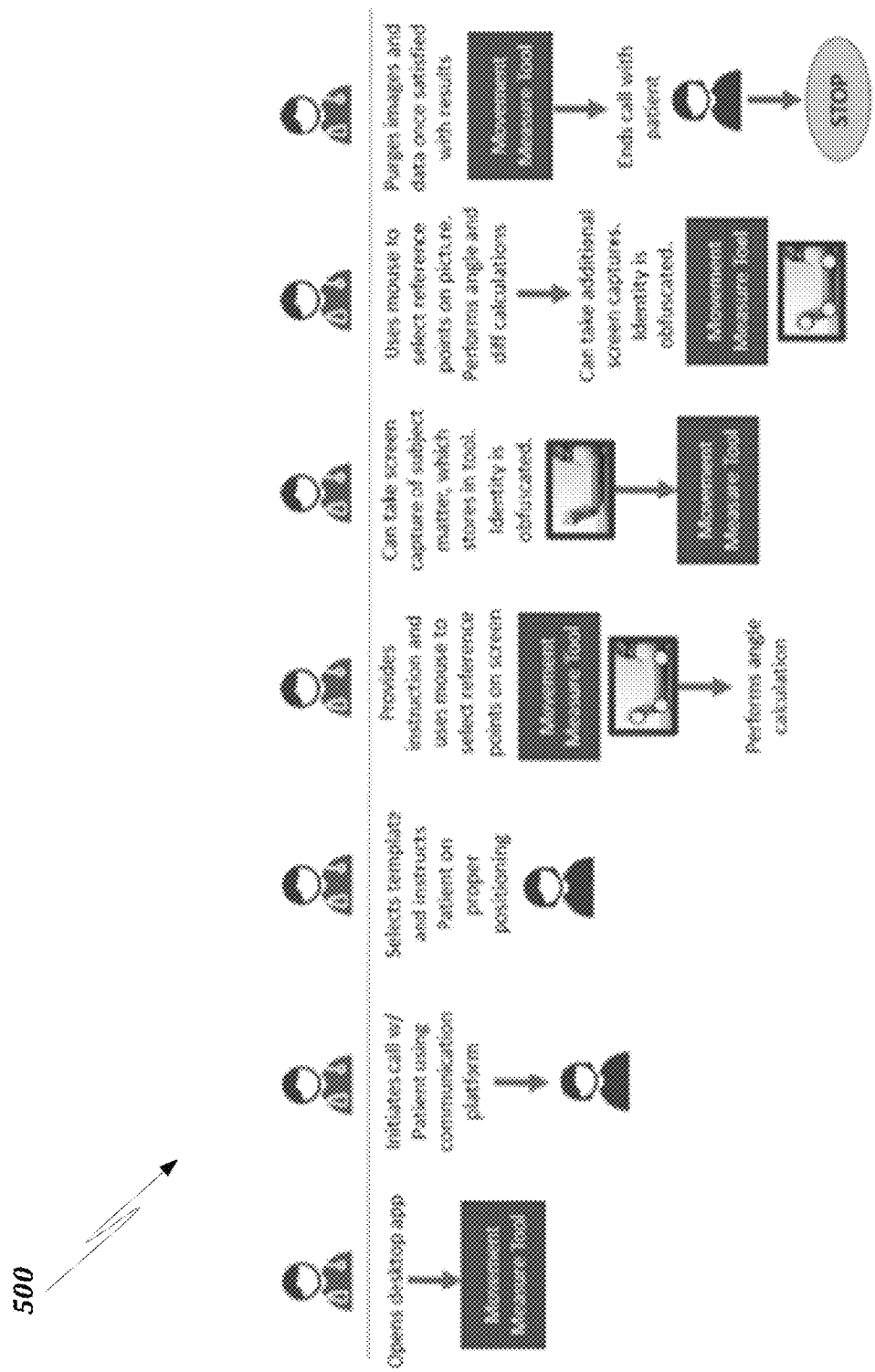
FIG. 5 is an example process flow using the platform of FIG. 1.

As a specific example, a process flowchart 500 is shown in FIG. 5. In the example process flow, the user (a health care professional) log in to a range of motion measurement application (e.g., the Movement Measure App). The user then initiates a call (e.g., a video call) with a patient using an external communication platform. The user instructs the patient on proper positioning for the range of motion testing. The user can select reference points corresponding to a joint of interest in the range of motion monitoring, and can take a screen capture of the patient in the proper position. The system can perform a calculation of the range of motion of the patient has in the joint of interest, based at least in part on the reference points selected by the user. Any screenshots take can be modified to obfuscate personally identifiable information. Images and data can be purged once the user is satisfied with the results, as part of exiting the app. The call between the user and the patient can be terminated, ending the process.

IV. Hardware Architecture

Embodiments of the present disclosure provide a hardware and software platform operative as a distributed system of modules and computing elements.

Platform 100 may be embodied as, for example, but not be limited to, a website, a web application, a desktop application, a backend application, and a mobile application compatible with a computing device 400. The computing device 400 may comprise, but not be limited to, the following:

Mobile computing device, such as, but is not limited to, a laptop, a tablet, a smartphone, a drone, a wearable, an embedded device, a handheld device, an Arduino, an industrial device, or a remotely operable recording device;

A supercomputer, an exascale supercomputer, a mainframe, or a quantum computer;

A minicomputer, wherein the minicomputer computing device comprises, but is not limited to, an IBM AS400/iSeries/System I, A DEC VAX/PDP, an HP3000, a Honeywell-Bull DPS, a Texas Instruments TI-990, or a Wang Laboratories VS Series;

A microcomputer, wherein the microcomputer computing device comprises, but is not limited to, a server, wherein a server may be rack-mounted, a workstation, an industrial device, a raspberry pi, a desktop, or an embedded device;

Platform 100 may be hosted on a centralized server or a cloud computing service. Although method 200 has been described to be performed by a computing device 400, it should be understood that, in some embodiments, different operations may be performed by a plurality of the computing devices 400 in operative communication on at least one network.

Embodiments of the present disclosure may comprise a system having a central processing unit (CPU) 420, a bus 430, a memory unit 440, a power supply unit (PSU) 450, and one or more Input/Output (I/O) units. The CPU 420 coupled to the memory unit 440 and the plurality of I/O units 460 via the bus 430, all of which are powered by the PSU 450. It should be understood that, in some embodiments, each disclosed unit may actually be a plurality of such units for redundancy, high availability, and/or performance purposes. The combination of the presently disclosed units is configured to perform the stages of any method disclosed herein.

Figure 4:
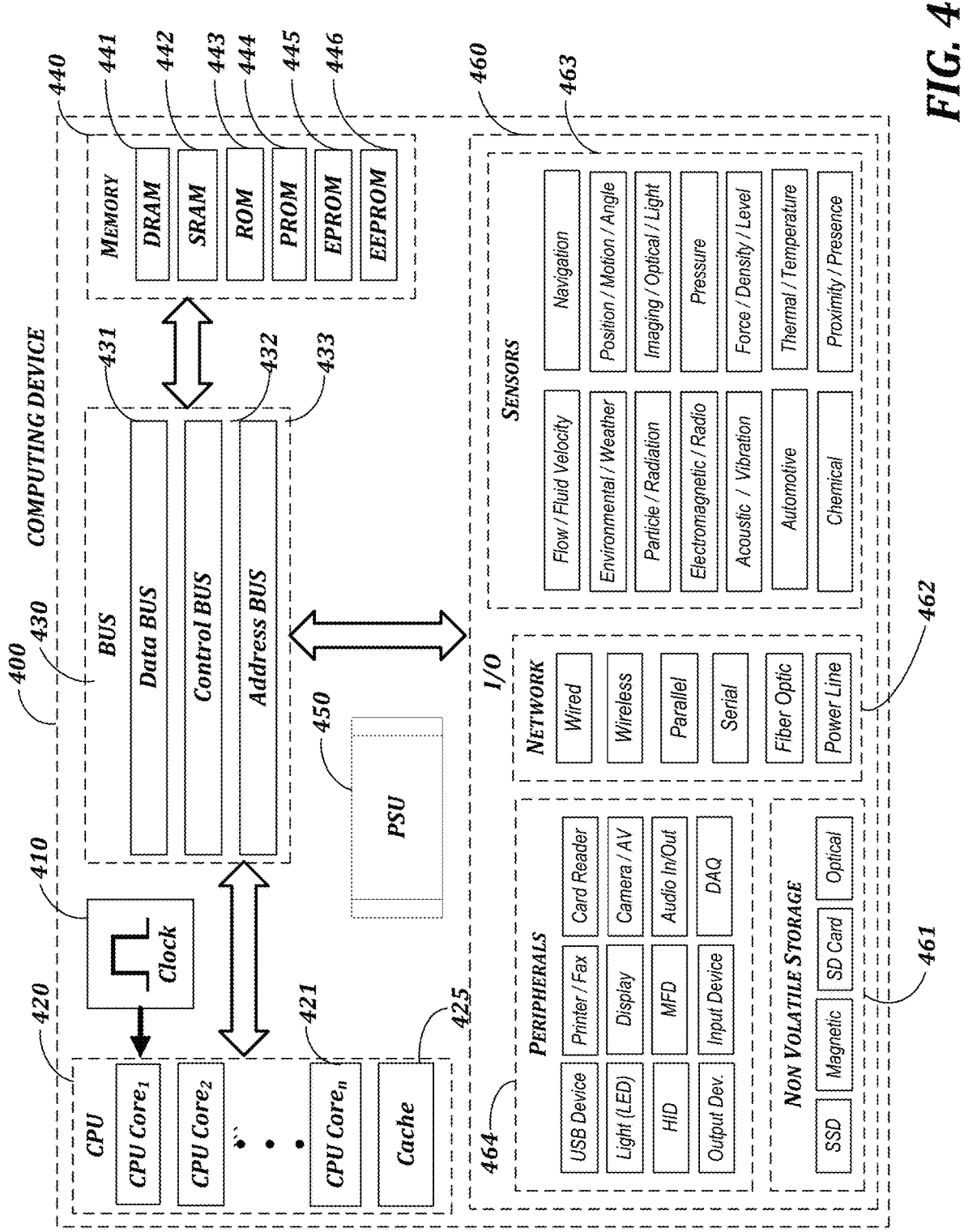
FIG. 4 is a block diagram of a system including a computing device for performing the method of FIG. 2.

FIG. 4 is a block diagram of a system including computing device 400. Consistent with an embodiment of the disclosure, the aforementioned CPU 420, the bus 430, the memory unit 440, a PSU 450, and the plurality of I/O units 460 may be implemented in a computing device, such as computing device 400 of FIG. 4. Any suitable combination of hardware, software, or firmware may be used to implement the aforementioned units. For example, the CPU 420, the bus 430, and the memory unit 440 may be implemented with computing device 400 or any of other computing devices 400, in combination with computing device 400. The aforementioned system, device, and components are examples and other systems, devices, and components may comprise the aforementioned CPU 420, the bus 430, and the memory unit 440, consistent with embodiments of the disclosure.

At least one computing device 400 may be embodied as any of the computing elements illustrated in all of the attached figures. A computing device 400 does not need to be electronic, nor even have a CPU 420, nor bus 430, nor memory unit 440. The definition of the computing device 400 to a person having ordinary skill in the art is "A device that computes, especially a programmable [usually] electronic machine that performs high-speed mathematical or logical operations or that assembles, stores, correlates, or otherwise processes information." Any device which processes information qualifies as a computing device 400, especially if the processing is purposeful.

With reference to FIG. 4, a system consistent with an embodiment of the disclosure may include a computing device, such as computing device 400. In some configurations, the computing device 400 may include at least one clock module 410, at least one CPU 420, at least one bus 430, and at least one memory unit 440, at least one PSU 450, and at least one I/O 460 module, wherein I/O module may be comprised of, but not limited to a non-volatile storage sub-module 461, a communication sub-module 462, a sensors sub-module 463, and a peripherals sub-module 464.

In a system consistent with an embodiment of the disclosure, the computing device 400 may include the clock module 410, known to a person having ordinary skill in the art as a clock generator, which produces clock signals. Clock signals may oscillate between a high state and a low state at a controllable rate, and may be used to synchronize or coordinate actions of digital circuits. Most integrated circuits (ICs) of sufficient complexity use a clock signal in order to synchronize different parts of the circuit, cycling at a rate slower than the worst-case internal propagation delays. One well-known example of the aforementioned integrated circuit is the CPU 420, the central component of modern computers, which relies on a clock signal. The clock 410 can comprise a plurality of embodiments, such as, but not limited to, a single-phase clock which transmits all clock signals on effectively 1 wire, a two-phase clock which distributes clock signals on two wires, each with non-overlapping pulses, and a four-phase clock which distributes clock signals on 4 wires.

Many computing devices 400 may use a "clock multiplier" which multiplies a lower frequency external clock to the appropriate clock rate of the CPU 420. This allows the CPU 420 to operate at a much higher frequency than the rest of the computing device 400, which affords performance gains in situations where the CPU 420 does not need to wait on an external factor (like memory 440 or input/output 460). Some embodiments of the clock 410 may include dynamic frequency change, where, the time between clock edges can vary widely from one edge to the next and back again.

In a system consistent with an embodiment of the disclosure, the computing device 400 may include the CPU 420 comprising at least one CPU Core 421. In other embodiments, the CPU 420 may include a plurality of identical CPU cores 421, such as, but not limited to, homogeneous multi-core systems. It is also possible for the plurality of CPU cores 421 to comprise different CPU cores 421, such as, but not limited to, heterogeneous multi-core systems, big.LITTLE systems and some AMD accelerated processing units (APU). The CPU 420 reads and executes program instructions which may be used across many application domains, for example, but not limited to, general purpose computing, embedded computing, network computing, digital signal processing (DSP), and graphics processing (GPU). The CPU 420 may run multiple instructions on separate CPU cores 421 simultaneously. The CPU 420 may be integrated into at least one of a single integrated circuit die, and multiple dies in a single chip package. The single integrated circuit die and/or the multiple dies in a single chip package may contain a plurality of other elements of the computing device 400, for example, but not limited to, the clock 410, the bus 430, the memory 440, and I/O 460.

The CPU 420 may contain cache 422 such as but not limited to a level 1 cache, a level 2 cache, a level 3 cache, or combinations thereof. The cache 422 may or may not be shared amongst a plurality of CPU cores 421. The cache 422 sharing may comprise at least one of message passing and inter-core communication methods used for the at least one CPU Core 421 to communicate with the cache 422. The inter-core communication methods may comprise, but not be limited to, bus, ring, two-dimensional mesh, and crossbar. The aforementioned CPU 420 may employ symmetric multiprocessing (SMP) design.

The one or more CPU cores 421 may comprise soft microprocessor cores on a single field programmable gate array (FPGA), such as semiconductor intellectual property cores (IP Core). The architectures of the one or more CPU cores 421 may be based on at least one of, but not limited to, Complex Instruction Set Computing (CISC), Zero Instruction Set Computing (ZISC), and Reduced Instruction Set Computing (RISC). At least one performance-enhancing method may be employed by one or more of the CPU cores 421, for example, but not limited to Instruction-level parallelism (ILP) such as, but not limited to, superscalar pipelining, and Thread-level parallelism (TLP).

Consistent with the embodiments of the present disclosure, the aforementioned computing device 400 may employ a communication system that transfers data between components inside the computing device 400, and/or the plurality of computing devices 400. The aforementioned communication system will be known to a person having ordinary skill in the art as a bus 430. The bus 430 may embody internal and/or external hardware and software components, for example, but not limited to a wire, an optical fiber, various communication protocols, and/or any physical arrangement that provides the same logical function as a parallel electrical bus. The bus 430 may comprise at least one of a parallel bus, wherein the parallel bus carries data words in parallel on multiple wires; and a serial bus, wherein the serial bus carries data in bit-wise serial form. The bus 430 may embody a plurality of topologies, for example, but not limited to, a multidrop/electrical parallel topology, a daisy chain topology, and connected by switched hubs, such as a USB bus. The bus 430 may comprise a plurality of embodiments, for example, but not limited to:

Internal data bus (data bus) 431/Memory bus
Control bus 432
Address bus 433
System Management Bus (SMBus)
Front-Side-Bus (FSB)
External Bus Interface (EBI)
Local bus
Expansion bus
Lightning bus
Controller Area Network (CAN bus)
Camera Link
ExpressCard
Advanced Technology management Attachment (ATA), including embodiments and derivatives such as, but not limited to, Integrated Drive Electronics (IDE)/Enhanced IDE (EIDE), ATA Packet Interface (ATAPI), Ultra-Direct Memory Access (UDMA), Ultra ATA (UATA)/Parallel ATA (PATA)/Serial ATA (SATA), CompactFlash (CF) interface, Consumer Electronics ATA (CE-ATA)/Fiber Attached Technology Adapted (FATA), Advanced Host Controller Interface (AHCI), SATA Express (SATAe)/External SATA (eSATA), including the powered embodiment eSATAp/Mini-SATA (mSATA), and Next Generation Form Factor (NGFF)/M.2.

Small Computer System Interface (SCSI)/Serial Attached SCSI (SAS)

HyperTransport

InfiniBand

RapidIO

Mobile Industry Processor Interface (MIPI)

Coherent Processor Interface (CAPI)

Plug-n-play

1-Wire

Peripheral Component Interconnect (PCI), including embodiments such as but not limited to, Accelerated Graphics Port (AGP), Peripheral Component Interconnect eXtended (PCI-X), Peripheral Component Interconnect Express (PCI-e) (e.g., PCI Express Mini Card, PCI Express M.2 [Mini PCIe v2], PCI Express External Cabling [ePCIe], and PCI Express OCuLink [Optical Copper{Cu} Link]), Express Card, AdvancedTCA, AMC, Universal IO, Thunderbolt/Mini DisplayPort, Mobile PCIe (M-PCIe), U.2, and Non-Volatile Memory Express (NVMe)/Non-Volatile Memory Host Controller Interface Specification (NVMHCIS).

Industry Standard Architecture (ISA), including embodiments such as, but not limited to Extended ISA (EISA), PC/XT-bus/PC/AT-bus/PC/104 bus (e.g., PC/104-Plus, PCI/104-Express, PCI/104, and PCI-104), and Low Pin Count (LPC).

Music Instrument Digital Interface (MIDI)

Universal Serial Bus (USB), including embodiments such as, but not limited to, Media Transfer Protocol (MTP)/Mobile High-Definition Link (MHL), Device Firmware Upgrade (DFU), wireless USB, InterChip USB, IEEE 1394 Interface/Firewire, Thunderbolt, and eXtensible Host Controller Interface (xHCI).

Consistent with the embodiments of the present disclosure, the aforementioned computing device 400 may employ hardware integrated circuits that store information for immediate use in the computing device 400, known to persons having ordinary skill in the art as primary storage or memory 440. The memory 440 operates at high speed, distinguishing it from the non-volatile storage sub-module 461, which may be referred to as secondary or tertiary storage, which provides relatively slower-access to information but offers higher storage capacity. The data contained in memory 440, may be transferred to secondary storage via techniques such as, but not limited to, virtual memory and swap. The memory 440 may be associated with addressable semiconductor memory, such as integrated circuits consisting of silicon-based transistors, that may be used as primary storage or for other purposes in the computing device 400. The memory 440 may comprise a plurality of embodiments, such as, but not limited to volatile memory, non-volatile memory, and semi-volatile memory. It should be understood by a person having ordinary skill in the art that the following are non-limiting examples of the aforementioned memory:

Volatile memory, which requires power to maintain stored information, for example, but not limited to, Dynamic Random-Access Memory (DRAM) 441, Static Random-Access Memory (SRAM) 442, CPU Cache memory 425, Advanced Random-Access Memory (A-RAM), and other types of primary storage such as Random-Access Memory (RAM).

Non-volatile memory, which can retain stored information even after power is removed, for example, but not limited to, Read-Only Memory (ROM) 443, Programmable ROM (PROM) 444, Erasable PROM (EPROM) 445, Electrically Erasable PROM (EEPROM) 446 (e.g., flash memory and Electrically Alterable PROM [EAPROM]), Mask ROM (MROM), One Time Programmable (OTP) ROM/Write Once Read Many (WORM), Ferroelectric RAM (FeRAM), Parallel Random-Access Machine (PRAM), Split-Transfer Torque RAM (STT-RAM), Silicon Oxime Nitride Oxide Silicon (SONOS), Resistive RAM (RRAM), Nano RAM (NRAM), 3D XPoint, Domain-Wall Memory (DWM), and millipede memory.

Semi-volatile memory may have limited non-volatile duration after power is removed but may lose data after said duration has passed. Semi-volatile memory provides high performance, durability, and other valuable characteristics typically associated with volatile memory, while providing some benefits of true non-volatile memory. The semi-volatile memory may comprise volatile and non-volatile memory, and/or volatile memory with a battery to provide power after power is removed. The semi-volatile memory may comprise, but is not limited to, spin-transfer torque RAM (STT-RAM).

Consistent with the embodiments of the present disclosure, the aforementioned computing device 400 may employ a communication system between an information processing system, such as the computing device 400, and the outside world, for example, but not limited to, human, environment, and another computing device 400. The aforementioned communication system may be known to a person having ordinary skill in the art as an Input/Output (I/O) module 460. The I/O module 460 regulates a plurality of inputs and outputs with regard to the computing device 400, wherein the inputs are a plurality of signals and data received by the computing device 400, and the outputs are the plurality of signals and data sent from the computing device 400. The I/O module 460 interfaces with a plurality of hardware, such as, but not limited to, non-volatile storage 461, communication devices 462, sensors 463, and peripherals 464. The plurality of hardware is used by at least one of, but not limited to, humans, the environment, and another computing device 400 to communicate with the present computing device 400. The I/O module 460 may comprise a plurality of forms, for example, but not limited to channel I/O, port mapped I/O, asynchronous I/O, and Direct Memory Access (DMA).

Consistent with the embodiments of the present disclosure, the aforementioned computing device 400 may employ a non-volatile storage sub-module 461, which may be referred to by a person having ordinary skill in the art as one of secondary storage, external memory, tertiary storage, off-line storage, and auxiliary storage. The non-volatile storage sub-module 461 may not be accessed directly by the CPU 420 without using an intermediate area in the memory 440. The non-volatile storage sub-module 461 may not lose data when power is removed and may be orders of magnitude less costly than storage used in memory 440. Further, the non-volatile storage sub-module 461 may have a slower speed and higher latency than in other areas of the computing device 400. The non-volatile storage sub-module 461 may comprise a plurality of forms, such as, but not limited to, Direct Attached Storage (DAS), Network Attached Storage (NAS), Storage Area Network (SAN), nearline storage, Massive Array of Idle Disks (MAID), Redundant Array of Independent Disks (RAID), device mirroring, off-line storage, and robotic storage. The non-volatile storage submodule (461) may comprise a plurality of embodiments, such as, but not limited to:

Optical storage, for example, but not limited to, Compact Disk (CD) (CD-ROM/CD-R/CD-RW), Digital Versatile Disk (DVD) (DVD-ROM/DVD-R/DVD+R/DVD-RW/DVD+RW/DVD±RW/DVD+R DL/DVD-RAM/HD-DVD), Blu-ray Disk (BD) (BD-ROM/BD-R/BD-RE/BD-R DL/BD-RE DL), and Ultra-Density Optical (UDO).

Semiconductor storage, for example, but not limited to, flash memory, such as, but not limited to, USB flash drive, Memory card, Subscriber Identity Module (SIM) card, Secure Digital (SD) card, Smart Card, CompactFlash (CF) card, Solid-State Drive (SSD) and memristor.

Magnetic storage such as, but not limited to, Hard Disk Drive (HDD), tape drive, carousel memory, and Card Random-Access Memory (CRAM).

Phase-change memory

Holographic data storage such as Holographic Versatile Disk (HVD).

Molecular Memory

Deoxyribonucleic Acid (DNA) digital data storage

Consistent with the embodiments of the present disclosure, the computing device 400 may employ a communication sub-module 462 as a subset of the I/O module 460, which may be referred to by a person having ordinary skill in the art as at least one of, but not limited to, a computer network, a data network, and a network. The network may allow computing devices 400 to exchange data using connections, which may also be known to a person having ordinary skill in the art as data links, which may include data links between network nodes. The nodes may comprise networked computer devices 400 that may be configured to originate, route, and/or terminate data. The nodes may be identified by network addresses and may include a plurality of hosts consistent with the embodiments of a computing device 400. Examples of computing devices that may include a communication sub-module 462 include, but are not limited to, personal computers, phones, servers, drones, and networking devices such as, but not limited to, hubs, switches, routers, modems, and firewalls.

Two nodes can be considered networked together when one computing device 400 can exchange information with the other computing device 400, regardless of any direct connection between the two computing devices 400. The communication sub-module 462 supports a plurality of applications and services, such as, but not limited to World Wide Web (WWW), digital video and audio, shared use of application and storage computing devices 400, printers/scanners/fax machines, email/online chat/instant messaging, remote control, distributed computing, etc. The network may comprise one or more transmission mediums, such as, but not limited to conductive wire, fiber optics, and wireless signals. The network may comprise one or more communications protocols to organize network traffic, wherein application-specific communications protocols may be layered, and may be known to a person having ordinary skill in the art as being improved for carrying a specific type of payload, when compared with other more general communications protocols. The plurality of communications protocols may comprise, but are not limited to, IEEE 802, ethernet, Wireless LAN (WLAN/Wi-Fi), Internet Protocol (IP) suite (e.g., TCP/IP, UDP, Internet Protocol version 4 [IPv4], and Internet Protocol version 6 [IPv6]), Synchronous Optical Networking (SONET)/Synchronous Digital Hierarchy (SDH), Asynchronous Transfer Mode (ATM), and cellular standards (e.g., Global System for Mobile Communications [GSM], General Packet Radio Service [GPRS], Code-Division Multiple Access [CDMA], Integrated Digital Enhanced Network [IDEN], Long Term Evolution [LTE], LTE-Advanced [LTE-A], and fifth generation [5G] communication protocols).

The communication sub-module 462 may comprise a plurality of size, topology, traffic control mechanisms and organizational intent policies. The communication sub-module 462 may comprise a plurality of embodiments, such as, but not limited to:

Wired communications, such as, but not limited to, coaxial cable, phone lines, twisted pair cables (ethernet), and InfiniBand.

Wireless communications, such as, but not limited to, communications satellites, cellular systems, radio frequency/spread spectrum technologies, IEEE 802.11 Wi-Fi, Bluetooth, NFC, free-space optical communications, terrestrial microwave, and Infrared (IR) communications. Wherein cellular systems embody technologies such as, but not limited to, 3G, 4G (such as WiMax and LTE), and 5G (short and long wavelength).

Parallel communications, such as, but not limited to, LPT ports.

Serial communications, such as, but not limited to, RS-232 and USB.

Fiber Optic communications, such as, but not limited to, Single-mode optical fiber (SMF) and Multi-mode optical fiber (MMF).

Power Line communications

The aforementioned network may comprise a plurality of layouts, such as, but not limited to, bus networks such as Ethernet, star networks such as Wi-Fi, ring networks, mesh networks, fully connected networks, and tree networks. The network can be characterized by its physical capacity or its organizational purpose. Use of the network, including user authorization and access rights, may differ according to the layout of the network. The characterization may include, but is not limited to a nanoscale network, a Personal Area Network (PAN), a Local Area Network (LAN), a Home Area Network (HAN), a Storage Area Network (SAN), a Campus Area Network (CAN), a backbone network, a Metropolitan Area Network (MAN), a Wide Area Network (WAN), an enterprise private network, a Virtual Private Network (VPN), and a Global Area Network (GAN).

Consistent with the embodiments of the present disclosure, the aforementioned computing device 400 may employ a sensors sub-module 463 as a subset of the I/O 460. The sensors sub-module 463 comprises at least one of the device, module, or subsystem whose purpose is to detect events or changes in its environment and send the information to the computing device 400. Sensors may be sensitive to the property they are configured to measure, may not be sensitive to any property not measured but be encountered in its application, and may not significantly influence the measured property. The sensors sub-module 463 may comprise a plurality of digital devices and analog devices, wherein if an analog device is used, an Analog to Digital (A-to-D) converter must be employed to interface the said device with the computing device 400. The sensors may be subject to a plurality of deviations that limit sensor accuracy. The sensors sub-module 463 may comprise a plurality of embodiments, such as, but not limited to, chemical sensors, automotive sensors, acoustic/sound/vibration sensors, electric current/electric potential/magnetic/radio sensors, environmental/weather/moisture/humidity sensors, flow/fluid velocity sensors, ionizing radiation/particle sensors, navigation sensors, position/angle/displacement/distance/speed/acceleration sensors, imaging/optical/light sensors, pressure sensors, force/density/level sensors, thermal/temperature sensors, and proximity/presence sensors. It should be understood by a person having ordinary skill in the art that the ensuing are non-limiting examples of the aforementioned sensors:

Chemical sensors, such as, but not limited to, breathalyzer, carbon dioxide sensor, carbon monoxide/smoke detector, catalytic bead sensor, chemical field-effect transistor, chemiresistor, electrochemical gas sensor, electronic nose, electrolyte-insulator-semiconductor sensor, energy-dispersive X-ray spectroscopy, fluorescent chloride sensors, holographic sensor, hydrocarbon dew point analyzer, hydrogen sensor, hydrogen sulfide sensor, infrared point sensor, ion-selective electrode, nondispersive infrared sensor, microwave chemistry sensor, nitrogen oxide sensor, olfactometer, optode, oxygen sensor, ozone monitor, pellistor, pH glass electrode, potentiometric sensor, redox electrode, zinc oxide nanorod sensor, and biosensors (such as nanosensors).

Automotive sensors, such as, but not limited to, air flow meter/mass airflow sensor, air-fuel ratio meter, AFR sensor, blind spot monitor, engine coolant/exhaust gas/cylinder head/transmission fluid temperature sensor, hall effect sensor, wheel/automatic transmission/turbine/vehicle speed sensor, airbag sensors, brake fluid/engine crankcase/fuel/oil/tire pressure sensor, camshaft/crankshaft/throttle position sensor, fuel/oil level sensor, knock sensor, light sensor, MAP sensor, oxygen sensor (O2), parking sensor, radar sensor, torque sensor, variable reluctance sensor, and water-in-fuel sensor.

Acoustic, sound and vibration sensors, such as, but not limited to, microphone, lace sensors such as a guitar pickup, seismometer, sound locator, geophone, and hydrophone.

Electric current, electric potential, magnetic, and radio sensors, such as, but not limited to, current sensor, Daly detector, electroscope, electron multiplier, faraday cup, galvanometer, hall effect sensor, hall probe, magnetic anomaly detector, magnetometer, magnetoresistance, MEMS magnetic field sensor, metal detector, planar hall sensor, radio direction finder, and voltage detector.

Environmental, weather, moisture, and humidity sensors, such as, but not limited to, actinometer, air pollution sensor, moisture alarm, ceilometer, dew warning, electrochemical gas sensor, fish counter, frequency domain sensor, gas detector, hook gauge evaporimeter, humistor, hygrometer, leaf sensor, lysimeter, pyranometer, pyrgeometer, psychrometer, rain gauge, rain sensor, seismometers, SNOTEL, snow gauge, soil moisture sensor, stream gauge, and tide gauge.

Flow and fluid velocity sensors, such as, but not limited to, air flow meter, anemometer, flow sensor, gas meter, mass flow sensor, and water meter.

Ionizing radiation and particle sensors, such as, but not limited to, cloud chamber, Geiger counter, Geiger-Muller tube, ionization chamber, neutron detection, proportional counter, scintillation counter, semiconductor detector, and thermoluminescent dosimeter.

Navigation sensors, such as, but not limited to, airspeed indicator, altimeter, attitude indicator, depth gauge, fluxgate compass, gyroscope, inertial navigation system, inertial reference unit, magnetic compass, MHD sensor, ring laser gyroscope, turn coordinator, variometer, vibrating structure gyroscope, and yaw rate sensor.

Position, angle, displacement, distance, speed, and acceleration sensors, such as but not limited to, accelerometer, displacement sensor, flex sensor, free-fall sensor, gravimeter, impact sensor, laser rangefinder, LIDAR, odometer, photoelectric sensor, position sensor such as, but not limited to, GPS or Glonass, angular rate sensor, shock detector, ultrasonic sensor, tilt sensor, tachometer, ultra-wideband radar, variable reluctance sensor, and velocity receiver.

Imaging, optical and light sensors, such as, but not limited to, CMOS sensor, colorimeter, contact image sensor, electro-optical sensor, infra-red sensor, kinetic inductance detector, LED configured as a light sensor, light-addressable potentiometric sensor, Nichols radiometer, fiber-optic sensors, optical position sensor, thermopile laser sensor, photodetector, photodiode, photomultiplier tubes, phototransistor, photoelectric sensor, photoionization detector, photomultiplier, photoresistor, photoswitch, phototube, scintillometer, Shack-Hartmann, single-photon avalanche diode, superconducting nanowire single-photon detector, transition edge sensor, visible light photon counter, and wavefront sensor.

Pressure sensors, such as, but not limited to, barograph, barometer, boost gauge, bourdon gauge, hot filament ionization gauge, ionization gauge, McLeod gauge, Oscillating U-tube, permanent downhole gauge, piezometer, Pirani gauge, pressure sensor, pressure gauge, tactile sensor, and time pressure gauge.

Force, Density, and Level sensors, such as, but not limited to, bhangmeter, hydrometer, force gauge or force sensor, level sensor, load cell, magnetic level or nuclear density sensor or strain gauge, piezocapacitive pressure sensor, piezoelectric sensor, torque sensor, and viscometer.

Thermal and temperature sensors, such as, but not limited to, bolometer, bimetallic strip, calorimeter, exhaust gas temperature gauge, flame detection/pyrometer, Gardon gauge, Golay cell, heat flux sensor, microbolometer, microwave radiometer, net radiometer, infrared/quartz/resistance thermometer, silicon bandgap temperature sensor, thermistor, and thermocouple.

Proximity and presence sensors, such as, but not limited to, alarm sensor, doppler radar, motion detector, occupancy sensor, proximity sensor, passive infrared sensor, reed switch, stud finder, triangulation sensor, touch switch, and wired glove.

Consistent with the embodiments of the present disclosure, the aforementioned computing device 400 may employ a peripherals sub-module 464 as a subset of the I/O 460. The peripheral sub-module 464 comprises ancillary devices uses to put information into and get information out of the computing device 400. There are 3 categories of devices comprising the peripheral sub-module 464, which exist based on their relationship with the computing device 400, input devices, output devices, and input/output devices. Input devices send at least one of data and instructions to the computing device 400. Input devices can be categorized based on, but not limited to:

Modality of input, such as, but not limited to, mechanical motion, audio, visual, and tactile.

Whether the input is discrete, such as but not limited to, pressing a key, or continuous such as, but not limited to the position of a mouse.

The number of degrees of freedom involved, such as, but not limited to, two-dimensional mice and three-dimensional mice used for Computer-Aided Design (CAD) applications.

Output devices provide output from the computing device 400. Output devices convert electronically generated information into a form that can be presented to humans. Input/output devices perform that perform both input and output functions. It should be understood by a person having ordinary skill in the art that the ensuing are non-limiting embodiments of the aforementioned peripheral sub-module 464:

Input Devices

Human Interface Devices (HID), such as, but not limited to, pointing device (e.g., mouse, touchpad, joystick, touchscreen, game controller/gamepad, remote, light pen, light gun, infrared remote, jog dial, shuttle, and knob), keyboard, graphics tablet, digital pen, gesture recognition devices, magnetic ink character recognition, Sip-and-Puff (SNP) device, and Language Acquisition Device (LAD).

High degree of freedom devices, that require up to six degrees of freedom such as, but not limited to, camera gimbals, Cave Automatic Virtual Environment (CAVE), and virtual reality systems.

Video Input devices are used to digitize images or video from the outside world into the computing device 400. The information can be stored in a multitude of formats depending on the user's requirement. Examples of types of video input devices include, but are not limited to, digital camera, digital camcorder, portable media player, webcam, Microsoft Kinect, image scanner, fingerprint scanner, barcode reader, 3D scanner, laser rangefinder, eye gaze tracker, computed tomography, magnetic resonance imaging, positron emission tomography, medical ultrasonography, TV tuner, and iris scanner.

Audio input devices are used to capture sound. In some cases, an audio output device can be used as an input device to capture produced sound. Audio input devices allow a user to send audio signals to the computing device 400 for at least one of processing, recording, and carrying out commands. Devices such as microphones allow users to speak to the computer to record a voice message or navigate software. Aside from recording, audio input devices are also used with speech recognition software. Examples of types of audio input devices include, but not limited to microphone, Musical Instrumental Digital Interface (MIDI) devices such as, but not limited to a keyboard, and headset.

Data AcQuisition (DAQ) devices convert at least one of analog signals and physical parameters to digital values for processing by the computing device 400. Examples of DAQ devices may include, but not limited to, Analog to Digital Converter (ADC), data logger, signal conditioning circuitry, multiplexer, and Time to Digital Converter (TDC).

Output Devices may further comprise, but not be limited to:

Display devices may convert electrical information into visual form, such as, but not limited to, monitor, TV, projector, and Computer Output Microfilm (COM). Display devices can use a plurality of underlying technologies, such as, but not limited to, Cathode-Ray Tube (CRT), Thin-Film Transistor (TFT), Liquid Crystal Display (LCD), Organic Light-Emitting Diode (OLED), MicroLED, E Ink Display (ePaper) and Refreshable Braille Display (Braille Terminal).

Printers, such as, but not limited to, inkjet printers, laser printers, 3D printers, solid ink printers, and plotters.

Audio and Video (AV) devices, such as, but not limited to, speakers, headphones, amplifiers, and lights, which include lamps, strobes, DJ lighting, stage lighting, architectural lighting, special effect lighting, and lasers.

Other devices such as Digital to Analog Converter (DAC)

Input/Output Devices may further comprise, but not be limited to, touchscreens, networking devices (e.g., devices disclosed in network sub-module 462), data storage devices (non-volatile storage 461), facsimile (FAX), and graphics/sound cards.

All rights, including copyrights in the code included herein, are vested in and the property of the Applicant. The Applicant retains and reserves all rights in the code included herein, and grants permission to reproduce the material only in connection with the reproduction of the granted patent and for no other purpose.

V. Claims

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as examples for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The invention claimed is:

1. One or more non-transitory computer readable media comprising instructions which, when executed by one or more hardware processors, causes performance of operations for monitoring range of motion in a joint of a patient, the operations comprising:

receiving video data from a communication platform, the video data comprising the joint of the patient;

determining that the patient is in position for calculating a range of motion of the joint;

capturing an image of the joint from the received video data;

receiving, from a user, selection of a first set of points used in measuring range of motion;

calculating a first angle measurement associated with the range of motion of the joint based on the selected set of points;

displaying the captured image together with an overlay comprising the first set of points and the first calculated angle;

and storing the captured image and the overlay to a storage device, wherein the storing comprises:

obfuscating the image to remove personally identified information from the image, wherein obfuscating the image does not alter the overlay, storing the obfuscated image and the unaltered overlay to the storage device, determining an end of an assessment session by a patient command, and purging the obfuscated image from storage based on the end of the assessment session by an input from the patient to the communication platform.

2. The non-transitory computer-readable media of claim 1, the operations further comprising:

capturing a second image of the joint from the received video datal receiving, from the user, selection of a second set of points used in measuring range of motion;

calculating a second angle measurement associated with the range of motion of the joint based on the second set of points;

and calculating an average angle based on the first angle measurement and the second angle measurement.

3. The non-transitory computer-readable media of claim 2, wherein each set of points used in measuring range of motion includes:

a first point associated with a first portion of a body of the patient, a second point associated with a second portion of the body of the patient, the second portion being movable relative to the first portion, and a third point associated with a fulcrum about which the second portion moves;

and wherein calculating the angle measurement associated with the range of motion of the joint comprises calculating an angle between the first point and the second point, measured about the fulcrum.

4. The non-transitory computer-readable media of claim 1, wherein the overlay comprises a set of angle indicia displayed in a circular pattern surrounding the joint.

5. The non-transitory computer-readable media of claim 1, wherein the video data is received from the communication platform via one or more Application Program Interfaces.

6. A method for monitoring range of motion in a joint of a patient's body, the method comprising:

receiving video data from a communication platform, the video data comprising the joint of the patient;

determining that the patient is in position for calculating a range of motion of the joint;

capturing an image of the joint from the received video data;

receiving, from a user, selection of a first set of points used in measuring range of motion;

calculating a first angle measurement associated with the range of motion of the joint based on the selected set of points;

displaying the captured image together with an overlay comprising the first set of points and the first calculated angle;

and storing the captured image and the overlay to a storage device, wherein the storing comprises:

obfuscating the image to remove personally identified information from the image, wherein obfuscating the image does not alter the overlay, storing the obfuscated image and the unaltered overlay to the storage device, determining an end of an assessment session by a patient command, and purging the obfuscated image from storage based on the end of the assessment session by an input from the patient to the communication platform;

wherein the method is performed by at least one device including a hardware processor.

7. The method of claim 6, further comprising:

capturing a second image of the joint from the received video data;

receiving, from the user, selection of a second set of points used in measuring range of motion;

calculating a second angle measurement associated with the range of motion of the joint based on the second set of points;

and calculating an average angle based on the first angle measurement and the second angle measurement.

8. The method of claim 7, wherein each set of points used in measuring range of motion includes:

a first point associated with a first portion of the patient's body, a second point associated with a second portion of the patient's body, the second portion being movable relative to the first portion, and a third point associated with a fulcrum about which the second portion moves;

and wherein calculating the angle measurement associated with the range of motion of the joint comprises calculating an angle between the first point and the second point, measured about the fulcrum.

9. The method of claim 6, wherein the overlay comprises a set of angle indicia displayed in a circular pattern surrounding the joint.

10. The method of claim 6, wherein the video data is received from the communication platform via one or more Application Program Interfaces.

11. A system for monitoring range of motion in a joint of a patient's body, the system comprising:

at least one device including a hardware processor;

the system being configured to perform operations comprising:

receiving video data from a communication platform, the video data comprising the joint of the patient;

determining that the patient is in position for calculating a range of motion of the joint;

capturing an image of the joint from the received video data;

receiving, from a user, selection of a first set of points used in measuring range of motion;

calculating a first angle measurement associated with the range of motion of the joint based on the selected set of points;

displaying the captured image together with an overlay comprising the first set of points and the first calculated angle;

and storing the captured image and the overlay to a storage device wherein the storing comprises:

obfuscating the image to remove personally identified information from the image, wherein obfuscating the image does not alter the overlay, storing the obfuscated image and the unaltered overlay to the storage device, determining an end of an assessment session by a patient command, and purging the obfuscated image from storage based on the end of the assessment session by an input from the patient to the communication platform.

12. The system of claim 11, the operations further comprising:

capturing a second image of the joint from the received video data;

receiving, from the user, selection of a second set of points used in measuring range of motion;

calculating a second angle measurement associated with the range of motion of the joint based on the second set of points;

and calculating an average angle based on the first angle measurement and the second angle measurement.

13. The system of claim 12, wherein each set of points used in measuring range of motion includes:
   a first point associated with a first portion of the patient's body, a second point associated with a second portion of the patient's body, the second portion being movable relative to the first portion, and a third point associated with a fulcrum about which the second portion moves;
   and wherein calculating the angle measurement associated with the range of motion of the joint comprises calculating an angle between the first point and the second point, measured about the fulcrum.

14. The system of claim 11, wherein the video data is received from the communication platform via one or more Application Program Interfaces.

* * * * *